US00PP12174P2

(12) United States Plant Patent
Grocholski

(10) Patent No.: US PP12,174 P2
(45) Date of Patent: Oct. 30, 2001

(54) COLEUS PLANT NAMED 'JAN'S GOLD'

(75) Inventor: Jan Grocholski, Franklin, WI (US)

(73) Assignee: City of Milwaukee, Milwaukee, WI (US)

( * ) Notice: Subject to any disclaimer, the term of this patent is extended or adjusted under 35 U.S.C. 154(b) by 0 days.

(21) Appl. No.: 09/271,735

(22) Filed: Mar. 18, 1999

(51) Int. Cl.[7] ..... A01H 5/00
(52) U.S. Cl. ..... Plt./373
(58) Field of Search ..... Plt./373

(56) References Cited

PUBLICATIONS

Jade Wizard Coleus, Park Seed Catalog, 1998–1999.

*Primary Examiner*—Bruce R. Campell
*Assistant Examiner*—June Hwu
(74) *Attorney, Agent, or Firm*—Michael Best & Friedrich LLP; Billie Jean Strandt

(57) ABSTRACT

A distinct variety of coleus characterized by its green and golden yellow color pattern on its folaige.

2 Drawing Sheets

FIELD OF THE INVENTION

The invention relates to a coleus plant, and, more particularly, to a new variety of coleus plant with a unique green and gold color pattern on the leaves.

BACKGROUND OF THE INVENTION

The coleus plant is an upright, self branching and easy to grow cultivar that is grown as an annual plant. It performs in full sun conditions and still retains its color. The coleus plant is generally easy to grow from new cuttings.

Coleus generally grows in a number of colors and shades varying from yellows, reds, oranges, greens and browns. One coleus in particular, 'Jade Wizard', includes ivory leaves edged in green.

SUMMARY OF THE INVENTION

The present invention is a coleus that differs from known varieties of coleus in the color pattern of its leaves. In particular, the present invention is a coleus that has green leaves edged in a golden yellow color.

BOTANICAL DESCRIPTION

Figure 1:
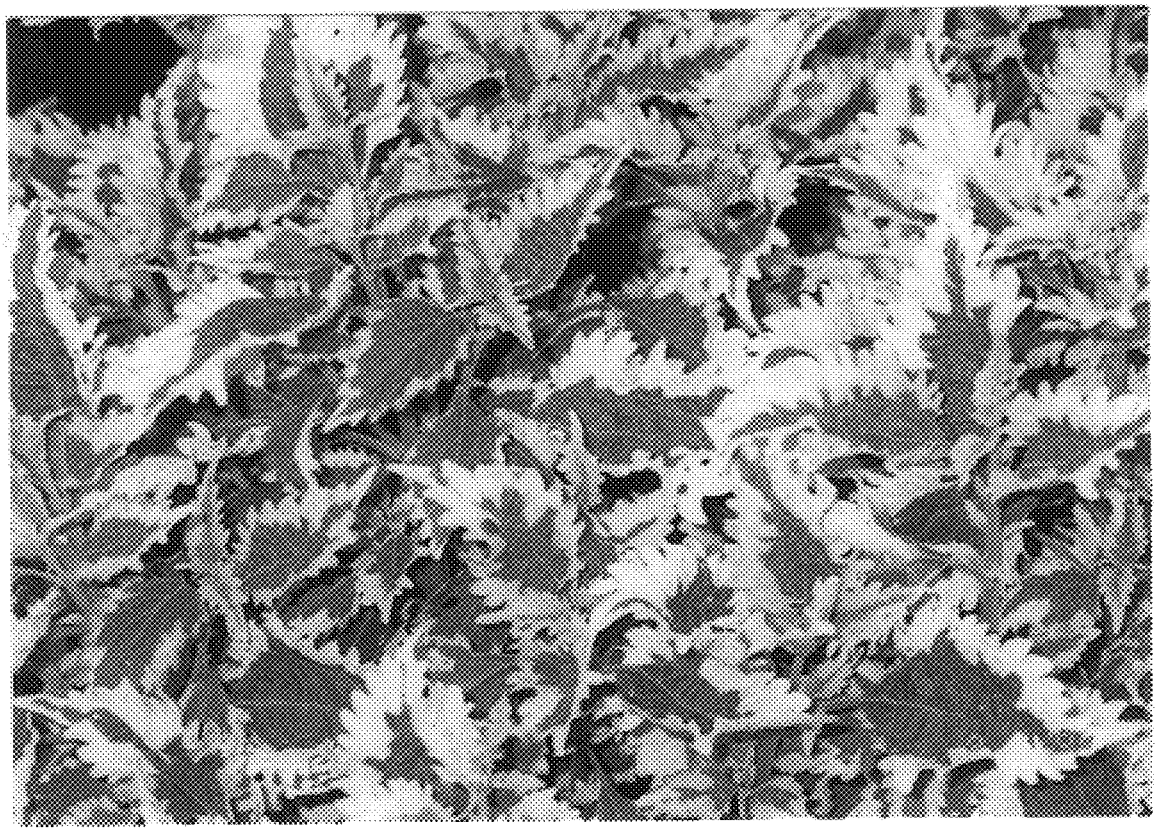
FIG. 1 depicts a plurality of mature specimens of the claimed coleus plant in an outdoor planting depicting the green and golden yellow color pattern of the leaves.
Figure 2:
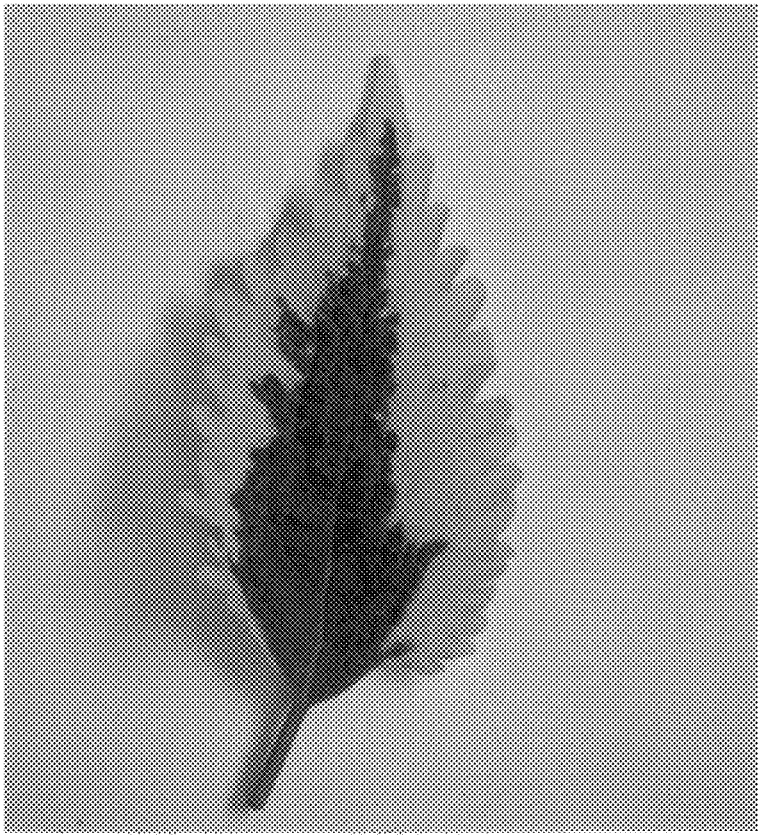
FIG. 2 shows the top surface of a leaf of the present invention illustrating the green and golden yellow color pattern.
Figure 3:
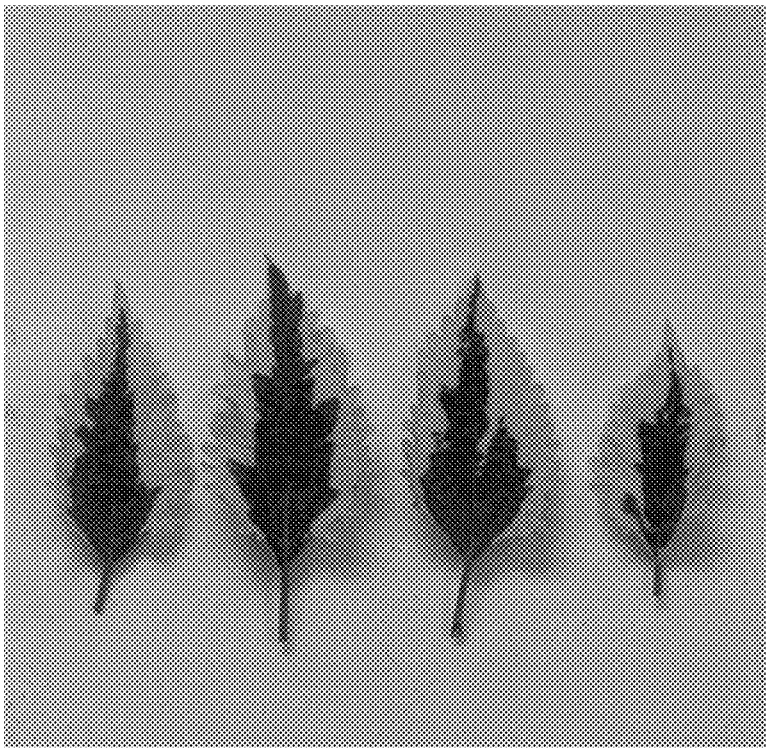
FIG. 3 shows the top surface of four leaves of the present invention illustrating the green and golden yellow color pattern.

With reference to FIGS. 1 through 3, the present variety of coleus is shown. The present variety of coleus was selected as a natural mutation of parent plant *Coleus*× *hybridus* 'Paisley Shaw', (not patented) grown in Franklin, Wis. The parent plant is an irregularly speckled variety consisting of the colors red and pink with a yellow and green colored background. A mutated cutting from the parent plant grown in a cultivated area in the City of Milwaukee Nursery Greenhouses was taken and a stock plant was grown and asexually propagated in the greenhouse. Subsequent cuttings were taken from the stock plant and propagated for three growing seasons. The plants, which were annuals, grew to an average height of about 40 cm in one growing season. The offspring have remained consistent in their color pattern and growing habits.

The present variety is a self branching cultivar, eliminating the need for pinching back. It is easy to propagate from stem and tip cuttings.

The leaf blades of the present variety are ovate 5–8 cm long and up to 3–6 cm wide. The leaf apex is cuspidate and the base is cuneate. Venaton of the leaf is pinnate with silverish pubescence.

While coleus plants generally grow in a number of colors and shades varying from yellows, reds, oranges, greens and browns, there are no know varieties that approach the green and gold pattern of the present variety. The color of the leaves of the present variety includes green (Royal Horticulture Society Colour Chart 137B) predominately in the center of each leaf and a golden yellow color (Royal Horticulture Society Colour Chart 9C and 9D) at the edging of the margins of the leaves. The R.H.S. colors on the underside of the leaves are the same as those on the top of the leaves. The margins of the leaves are cleft serrated and sometimes dotted with the green (Royal Horticulture Society Colour Chart 137B). Petioles are round, 2–4 cm long when mature with the diameter of 2 mm. The color of the petiole is green (Royal Horticulture Society Colour Chart 137B) and new shoot growth is apparent at each leaf axil.

The stems of the present variety are green (Royal Horticulture Society Colour Chart 137B) with a diameter of 5–9 mm at maturity. Internode length ranges from 2 to 6 cm. In cross section, the stems are square.

The inflorescence is a typical raceme for the genus. The pale blue (Royal Horticulture Society Colour Chart 133D) flowers do not produce seeds.

The height of present variety coleus plant reaches 40 cm in average growing conditions.

Plant diseases and pest resistance or susceptibility has not been observed to date on plants of new Coleus.

I claim:

1. A new and distinct variety of coleus plant substantially as herein shown and described, characterized by its green leaves with golden yellow edging.

* * * * *